(12) United States Patent
Chin

(10) Patent No.: US 6,749,601 B2
(45) Date of Patent: Jun. 15, 2004

(54) PROTECTIVE SLEEVE FOR AN ENDOSCOPIC INSTRUMENT AND RELATED METHOD OF USE

(75) Inventor: Yem Chin, Burlington, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/920,809

(22) Filed: Aug. 3, 2001

(65) Prior Publication Data

US 2003/0028178 A1 Feb. 6, 2003

(51) Int. Cl.[7] ............................................. A61B 17/00
(52) U.S. Cl. .......................... 606/1; 600/124; 206/363
(58) Field of Search ............................... 600/121–125; 206/363, 306; 604/171, 172, 164.05; 606/1

(56) References Cited

U.S. PATENT DOCUMENTS

| 4,593,699 | A | * | 6/1986 | Poncy et al. ................ 600/459 |
| 4,772,275 | A | * | 9/1988 | Erlich ......................... 604/523 |
| 4,936,304 | A | * | 6/1990 | Kresh et al. .................. 607/23 |
| 4,946,440 | A | * | 8/1990 | Hall ....................... 604/164.09 |
| 5,228,851 | A | * | 7/1993 | Burton ....................... 433/116 |
| 5,647,857 | A | * | 7/1997 | Anderson et al. ........... 604/264 |
| 5,765,682 | A | * | 6/1998 | Bley et al. ................... 206/363 |
| 5,938,586 | A | * | 8/1999 | Wilk et al. .................. 600/123 |
| 6,027,480 | A | * | 2/2000 | Davis et al. ............ 604/164.05 |
| 6,051,293 | A | * | 4/2000 | Weilandt .................... 428/35.2 |
| 6,224,543 | B1 | | 5/2001 | Gammons et al. |
| 2001/0049499 | A1 | * | 12/2001 | Lui et al. ............... 604/164.05 |
| 2002/0156344 | A1 | | 10/2002 | Pasricha et al. |

FOREIGN PATENT DOCUMENTS

| EP | 0452123 A1 | * | 10/1991 | ........... A61L/29/00 |
| EP | 1129674 A1 | * | 9/2001 | ............. A61F/2/06 |

* cited by examiner

*Primary Examiner*—John P. Leubecker
(74) *Attorney, Agent, or Firm*—Finnegan Henderson Farabow Garrett & Dunner, L.L.P.

(57) ABSTRACT

A protective sleeve for use with an endoscopic surgical instrument is provided. The protective sleeve includes a flexible tube having an opening at each end of the tube and a length to cover a desired portion of the surgical instrument. At one end of the tube may be an elastic band that allows the sleeve to be positioned over the instrument or to be retracted to reveal the instrument for use. Additionally, the tube may also include a second band that may be fixed or movable. The tube also may have a perforation running along the length of the tube to allow for the sleeve to be easily removed from the instrument. A circumferential perforation may also be provided. A method for using the protective sleeve is also provided.

46 Claims, 4 Drawing Sheets

PROTECTIVE SLEEVE FOR AN ENDOSCOPIC INSTRUMENT AND RELATED METHOD OF USE

DESCRIPTION OF THE INVENTION

Field of the Invention

The invention relates to an endoscopic surgical instrument. More particularly, the invention relates to a protective sleeve to cover, for example, any potentially damaging protrusions or rough edges on such an instrument, and a related method of using that protective sleeve in an endoscopic procedure.

BACKGROUND OF THE INVENTION

An endoscopic surgical procedure is one of the lesser invasive surgical procedures available to treat many disorders. In an exemplary endoscopic procedure, an endoscope and/or other instruments is inserted into a body lumen, such as, for example, the esophagus. The operator guides the endoscope and instruments through the lumen until they reach the location within the patient where a surgical procedure is to be performed. Once the instruments are in position, the operator uses controls connected to the various instruments, but located outside the patient, to perform the desired procedure.

Some endoscopic procedures involve the introduction of a tube into the body lumen having passages through which other instruments are inserted, thus protecting the patient from any rough edges or protruding portions on those instruments. In other procedures, the instruments may be inserted directly into the body lumen itself. These instruments may include tools such as graspers, cutters, staplers, biopsy devices, etc., that can impinge upon and damage tissue as they are inserted and guided through the lumen to the location of the procedure to be performed.

An exemplary endoscopic procedure treats gastroesophageal reflux disease. Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as gastroesophageal reflux disease (GERD).

A surgical procedure has been developed to prevent acid reflux in patients whose normal lower esophageal sphincter functioning has been impaired. This procedure, a Nissen fundoplication, involves bringing the fundus into closer proximity to the esophagus and suturing the fundus thereto, to help close off the esophageal opening into the stomach. Traditionally, this procedure has been performed as an open surgery, but also has been performed laparoscopically and endoscopically.

Less invasive endoscopic treatments of gastroesophageal reflux disease may utilize a remotely operable invagination device and a remotely operable surgical stapler, both of which are inserted transorally through the esophagus. The invagination device may be inserted first and used to clamp the gastroesophageal junction. The device is then moved distally, pulling the clamped gastroesophageal junction into the stomach, thereby invaginating the junction and involuting the surrounding fundic wall. The stapler then may be inserted transorally and delivered to the invaginated junction where it is used to staple the fundic wall. The stapling device must apply sufficient force to pierce the tissue that is to be fastened.

While the stapling device, grasper, and other instruments are often compact, they may contain edges or protrusions that could contact tissue as the device is inserted transorally. As these tools are inserted directly into the esophagus, they may impinge upon tissue and cause damage along the insertion path. Once the procedure has been performed, the same difficulty may be encountered in the removal of the various instruments.

This problem of damaging tissue during instrument insertion applies not only to GERD treatment procedures but also to many other endoscopic surgical procedures. The GERD treatment has been described as an example. Insertion of any endoscopic tool with rough edges or sharp protrusions through a body lumen has the potential for damage to the tissue along the path. Preventing this potential for damage would benefit endoscopic procedures.

SUMMARY OF THE INVENTION

In accordance with an aspect of the invention, a protective sleeve is provided for use with an endoscopic surgical instrument. The protective sleeve includes a flexible tube having an opening at each end of the tube and of a length to cover a desired portion of the surgical instrument. In addition, an elastic ring is provided proximate one end of the tube.

In accordance with another aspect of the invention, the protective sleeve is provided with a perforation running the length of the tube.

In accordance with yet another aspect of the invention, the flexible tube is transparent.

In accordance with another aspect of the invention, the protective sleeve further includes a ring of a fixed diameter located at the opposite end of the tube from the elastic band. In addition, a circumferential perforation is provided at the end of the tube with the fixed diameter ring.

In accordance with another aspect of the invention, the protective sleeve further includes a second elastic ring located opposite the first elastic ring.

In accordance with another aspect of the invention, the sleeve is folded in on itself and a third ring is added to affix the end of the sleeve at a point proximal to the distal end of the instrument and the second ring is located at the fold of the sleeve.

In accordance with another aspect of the invention, the sleeve further includes a pocket at the distal end of the sleeve to house the second and third rings.

In accordance with an additional aspect of the invention, the flexible tube may be coated with a lubricating material.

In accordance with yet another aspect of the invention, a method for using the protective sleeve in conjunction with a surgical instrument is provided wherein a protective sleeve is provided over a distal portion of the surgical instrument. The instrument is then inserted into a body lumen and placed in a desired location along the lumen. A distal end of the protective sleeve is then moved toward a proximal end of the sleeve to reveal the instrument.

In accordance with another aspect of the invention, a surgical procedure is then performed and the sleeve is moved back into position over the distal end of the surgical instrument. The instrument is then removed from the body lumen.

In accordance with another aspect of the invention, the protective sleeve is removed entirely from the instrument by tearing the sleeve along one or more perforations located along the length of the sleeve.

In accordance with yet another aspect of the invention, a fixed ring is used to hold the proximal end of the sleeve in place and the sleeve is removed by additionally tearing the sleeve along a circumferential perforation located at the same end of the sleeve as the fixed band.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

Figure 1:
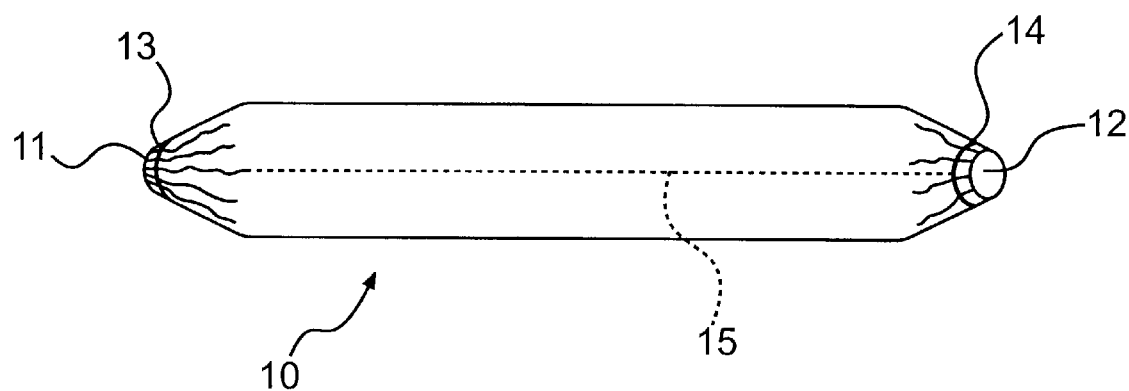
FIG. 1 is a view of a protective sleeve according to an embodiment of the present invention.

FIG. 1 shows a protective sleeve 10 according to an embodiment of the present invention. Sleeve 10 is constructed to cover the working components at a distal end of an endoscope and to retract to expose those working components so that a surgical procedure may be performed, as will be explained further herein. Sleeve 10 is provided with two open ends 11, 12. Sleeve 10 is essentially cylindrical in shape and is made of a thin layer of protective, biocompatible material, such as polyethylene or vinyl, for example, or any other suitable material known in the art, including any resin material. The material preferably is sufficiently flexible to cover the working components of the endoscopic device and to retract to expose those components. The material, however, should have sufficient strength to resist tearing from sharp edges or protrusions from the endoscopic instrument that it covers. In addition, the surface of sleeve 10 may be coated with a hydrogel or other lubricating material known in the art to allow for easier passage within an esophagus or other body lumen. Sleeve 10 also may be made of a translucent material to allow for easier and more precise positioning by being able to see the exact location of the working components, or tool, contained in the sleeve in relation to the patient. Such viewing may be performed by any suitable method known in the art for viewing an endoscopic instrument inside the body, including using an internal endoscope with an optical system or any external viewing method. Sleeve 10 can be made of a flat tubing material that can be cut to length to allow the sleeve to cover any length of surgical device desired. In addition, varying diameters of sleeve material can be used so that sleeve 10 can cover a range of sizes of surgical devices.

Sleeve 10 also may be provided with one or more perforations 15 running along the length of sleeve 10 to allow for easy removal by either tearing or cutting along the perforation and separating the sleeve from the device it is covering. In one exemplary embodiment, sleeve 10 includes two perforations 15 on opposite sides of sleeve 10.

Sleeve 10 also includes two or more expandable bands and/or rings 13, 14 to hold the ends 11, 12 of sleeve 10 in place on the endoscopic device. Rings 13, 14 are preferably made of an elastic material and have a size and flexibility so that rings 13, 14 close sleeve 10 over an endoscopic device. Rings 13, 14 also allow sleeve 10 to be retracted towards the proximal end to expose only the portions of the endoscopic device needed for a surgical procedure. Rings 13, 14 also may be made of a material that can be severed by traditional surgical instruments so that the entirety of sleeve 10 may be removed, if desired, by cutting rings 13, 14 and tearing along perforation or perforations 15 to separate sleeve 10 from the device it encloses. In addition, while proximal ring 13 may be an expandable elastic band, it may be desirable to affix ring 13 to endoscope 20 by a weld or other affixing means known in the medical field.

Figure 2:
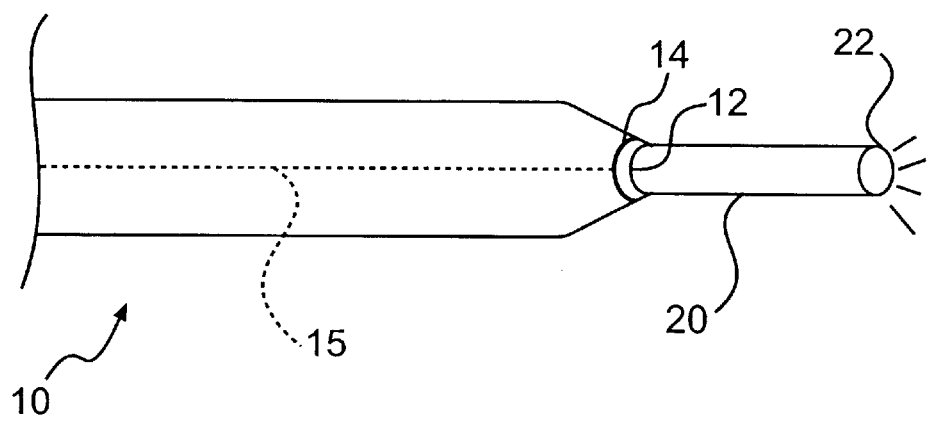
FIG. 2 is a partial view of the protective sleeve of FIG. 1 extended on a distal end of a GERD device, with an optical portion of an endoscope protruding from the sleeve, according to an embodiment of the present invention.

FIG. 2 shows protective sleeve 10 in place over an endoscope 20 and containing an associated instrument (not pictured) within the sleeve. The optical end 22 of endoscope 20 is depicted protruding through opening 12 so that the operator may view the insertion path as endoscope 20 is guided along a body lumen until it reaches the location of the procedure to be performed.

Figure 3:
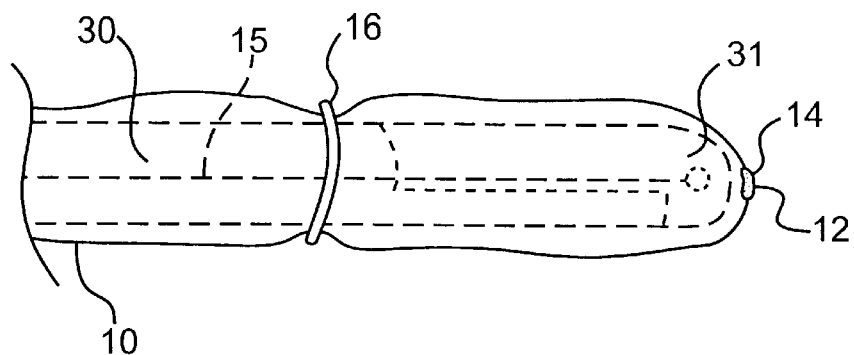
FIG. 3 is a view of a protective sleeve according to an embodiment of the invention in place over the distal end of a GERD device, with a ring positioned to provide a stop for the retraction of the sleeve.

FIG. 3 is a view of protective sleeve 10 in place over a distal end of a GERD device 30 (shown by dashed lines) to allow the device to be used in a surgical procedure, according to an embodiment of the present invention. GERD device 30, in this embodiment, includes a stapling mechanism 31 at its distal end. While protective sleeve 10 will be described in use with an endoscope and device 30 with stapling mechanism 31 for use in a GERD procedure, a protective sleeve according to the present invention may be used in combination with any endoscopic surgical instrument to protect a body lumen from potentially harmful edges or protrusions on the instrument as the instrument is introduced into the patient.

Figure 4:
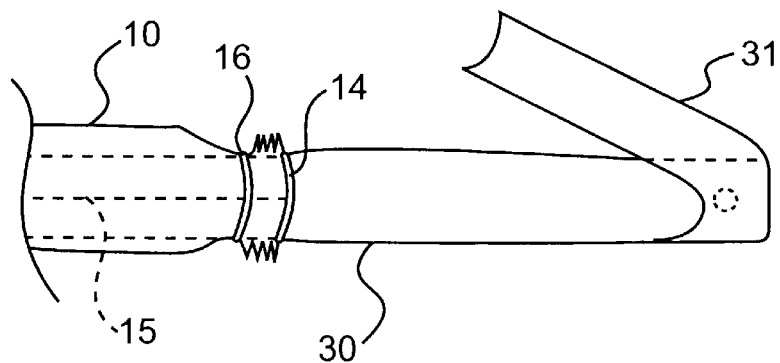
FIG. 4 is a view of the protective sleeve of FIG. 3 retracted in an accordion-like fashion to expose the distal end of the GERD device to allow the device to be used in a surgical procedure, according to an embodiment of the present invention.

Sleeve 10 is shown in FIG. 3 with a very small opening 12 in a distal end of sleeve 10. In this embodiment, ring 14 is sufficiently elastic to substantially close so that sleeve 10 fully encloses GERD device 30 within sleeve 10. Though not shown in FIGS. 3–7, a ring would preferably still be used to fix the proximal end of the sleeve to the endoscopic device. In addition, this embodiment of sleeve 10 includes a third ring 16 fixed in a position along the length of sleeve 10 and preferably near a middle portion of sleeve 10. As sleeve 10 is retracted proximally as shown in FIG. 4, ring 14 approaches the position of ring 16. Ring 16 allows sleeve 10 to retract in an accordion-like fashion against ring 16. As shown in FIG. 4, stapling device 31 has been exposed by retracting sleeve 10 and is in a deployed position to staple tissue.

If it is desirable to remove sleeve 10 altogether, sleeve 10 may be cut or torn along perforation 15. Additional perforations may be provided along the length of sleeve 10 to allow sleeve 10 to peel back in a proximal direction, much like a banana peel is removed to expose a banana. Rings 13, 14, and 16 may be either cut or provided with a notch or notches that allow the rings to break when excessive force is applied. This permits the rings and sleeve 10 to be removed.

Figure 5:
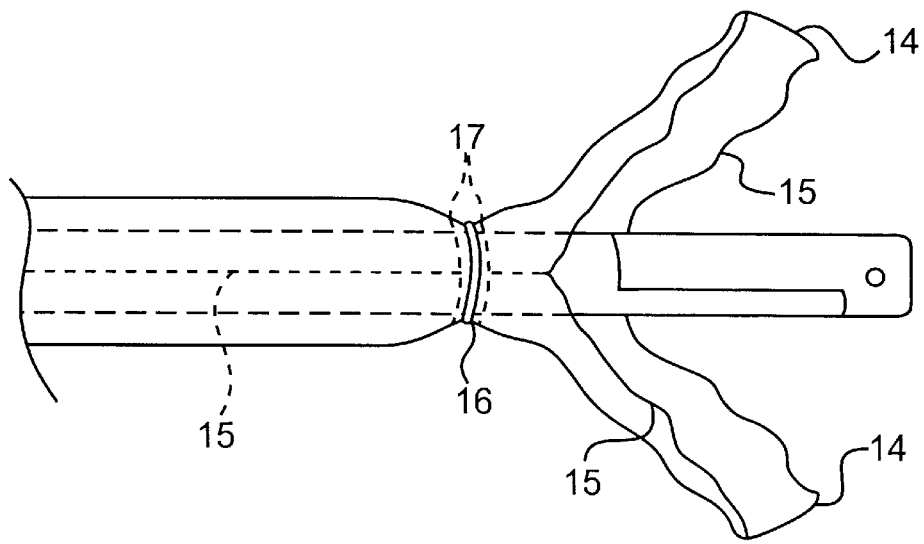
FIG. 5 is a view of a protective sleeve according to an embodiment of the invention torn along two perforation lines.

In an alternative embodiment shown in FIG. 5, sleeve 10 includes circumferential perforations 17 that permit band 16 to remain on GERD device 30, but will allow sleeve 10 to be removed from band 16. As shown in FIG. 5, band 14 has split and sleeve 10 is broken along perforations 15 on both sides of sleeve 10. Once sleeve 10 has been peeled back to perforation 17 on the distal side of ring 16, sleeve 10 may be torn along circumferential perforation 17 to remove the portion of sleeve 10 distal to ring 16.

Figure 6A:
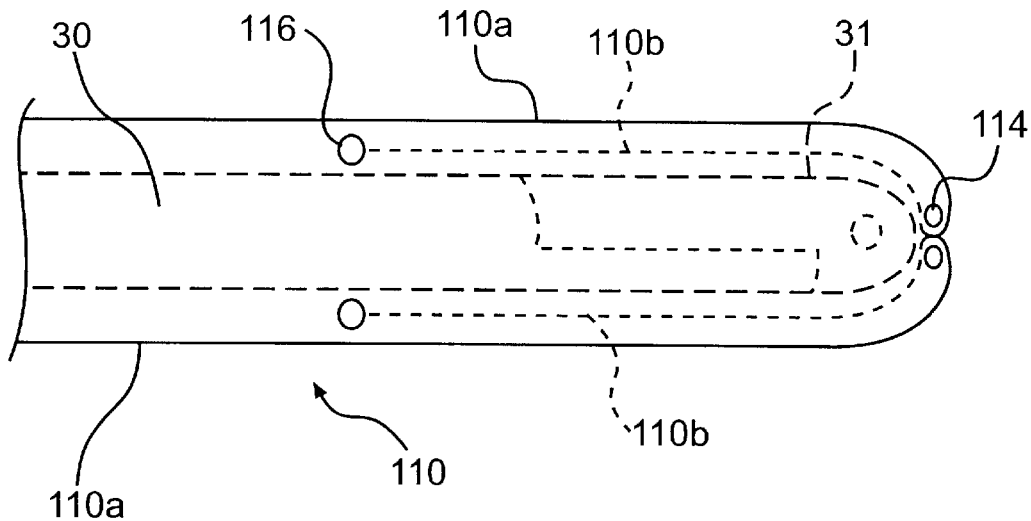
FIG. 6A shows another embodiment of a protective sleeve according to the present invention, where the sleeve is folded onto itself at the distal end.

According to another embodiment shown in FIG. 6A, protective sleeve 110 is doubled back, or in other words, folded onto itself, at the distal end of sleeve 110. In this way, when sleeve 110 is covering GERD device 30 and its stapling mechanism 31, sleeve 110 has an outer exposed sleeve portion 110a (shown by the solid line in FIG. 6A) and an inner sleeve portion 110b (shown by a dashed line in FIG. 6A) that is covered by sleeve portion 110a. The end of sleeve 110 is affixed to GERD device 30 by a ring 116 at a point along GERD device 30 that will allow stapling mechanism 31 to be exposed for use when the sleeve 110 is retracted. Ring 116 is preferably fixed to GERD device 30 by means of a surgical weld or other suitable means known in the art to fix ring 116 permanently in place.

Figure 6B:
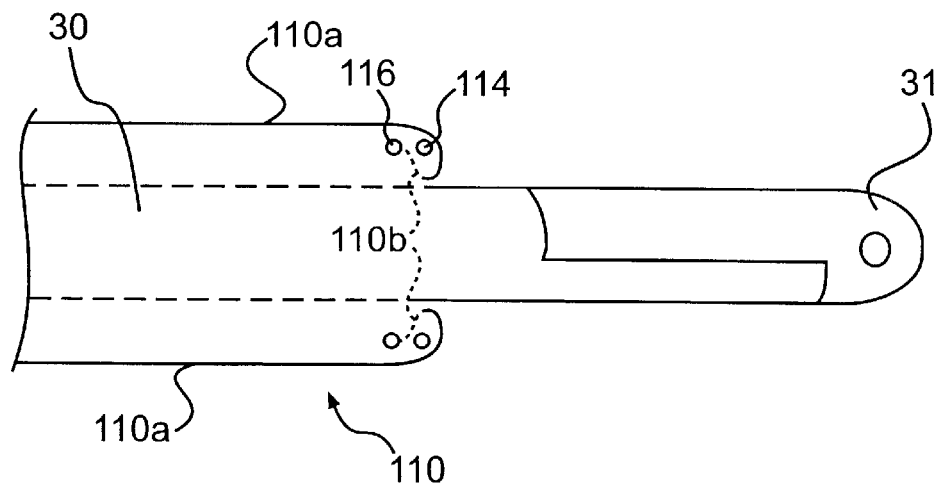
FIG. 6B shows the protective sleeve of FIG. 6A in a retracted position.

In this configuration, an operator retracts sleeve 110 to reveal stapling mechanism 31 by pulling on the proximal end of sleeve 110 (not shown in the Figures) with a surgical grasper or other similar device. As sleeve 110 is pulled, ring 114 expands around stapling mechanism 31 to reveal mechanism 31 and rolls over the fold of sleeve 110, i.e. sleeve portion 110b, until ring 114 comes into proximity with ring 116, as shown in FIG. 6B.

Figure 7A:
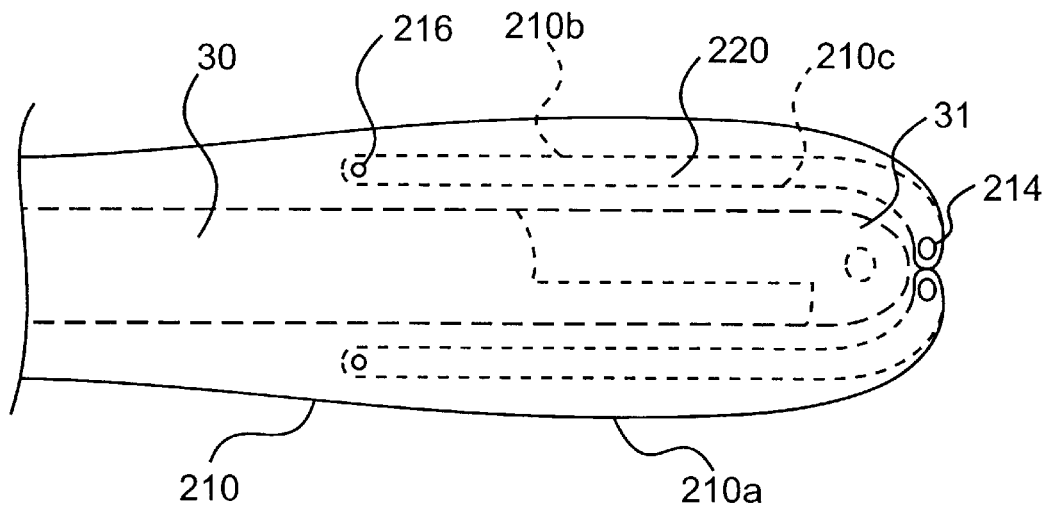
FIG. 7A shows another embodiment of a protective sleeve according to the present invention, where a pocket is created within the end of the sleeve.
Figure 7B:
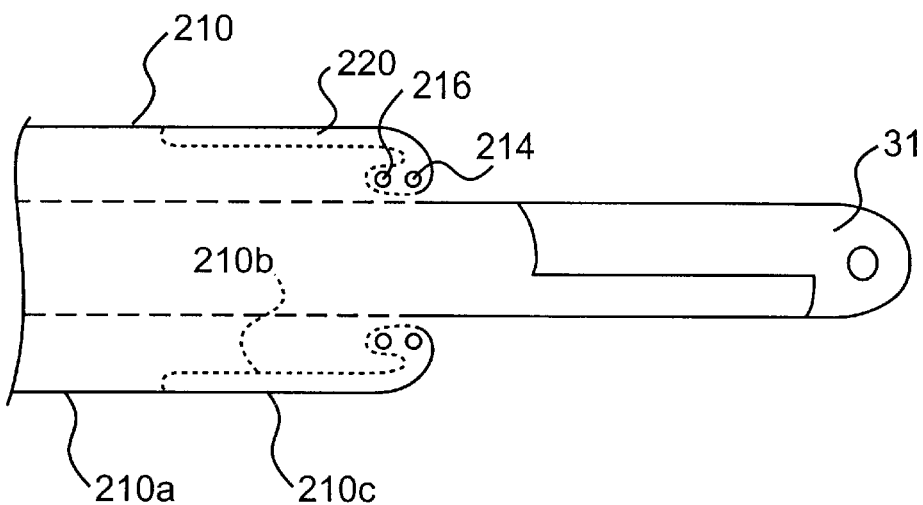
FIG. 7B shows the protective sleeve of FIG. 7A in a retracted position.

FIGS. 7A and 7B show a variation of the embodiment shown and described with reference to FIGS. 6A and 6B. In FIG. 7A, a pocket 220 is formed within the end of sleeve 210. Pocket 220 could be formed by doubling the distal end of sleeve 210 back on itself and welding the end in place at a point proximal the end of the sleeve. Pocket 220 could also be formed by welding a separate sleeve piece inside sleeve 210 to create essentially the same pocket. Sleeve 210 is folded onto itself as in the previous embodiment, but in this configuration, rings 214 and 216 are enclosed within pocket 220. When the sleeve 210 encloses the endoscopic device 30, as seen in FIG. 7A, sleeve 210 includes an outer sleeve portion 210a further includes two inner sleeve portions 210b and 210c that make up the walls of pocket 220. As sleeve 210 is retracted to the position shown in FIG. 7B, pocket 220 doubles back, or folds, on itself, and sleeve portion 210c becomes exposed. As with sleeve 110, a ring 216 is preferably affixed to GERD device 30. A ring 214 is free to move within pocket 220. Sleeve 210 is retracted in essentially the same fashion as sleeve 210. An operator pulls on the proximal end of sleeve 210, causing ring 214 to roll toward ring 216, eventually revealing stapling mechanism 31 to be used in the desired surgical procedure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A protective sleeve for use with an endoscopic surgical instrument, comprising:

a flexible tube having an opening at each end of a proximal end and a distal end of the tube, the tube having a length and being configured to cover at least a distal portion of the surgical instrument that reaches a treatment site in a body lumen; and a distal ring fixedly connected to the tube proximate the distal end of the tube and being sufficiently elastic to substantially close the opening at the distal end of the tube, the distal ring configured to be retractable in a proximal direction relative to the surgical instrument and thereby allow at least a portion of the tube to retract and reveal a distal end portion of the surgical instrument.

2. The protective sleeve of claim 1, further comprising at least one perforation located along the length of the tube.

3. The protective sleeve of claim 1, wherein the flexible tube is translucent.

4. The protective sleeve of claim 1, further comprising a second ring positioned at a location along the tube in a direction proximal relative to the distal ring, the distal ring being configured to be retractable towards the second ring.

5. The protective sleeve of claim 1, further comprising a perforation about a circumference of the tube.

6. The protective sleeve of claim 1, further comprising a proximal ring proximate the proximal end of the tube.

7. The protective sleeve of claim 6, further comprising a third ring located between the proximal and distal rings.

8. The protective sleeve of claim 1, further comprising:

a second ring positioned at a location along the tube in a direction proximal relative to the distal ring, wherein the flexible tube comprises an inner tube portion and an outer tube portion; and the distal ring is located at a point where the inner and outer tube portions meet.

9. The protective sleeve of claim 8, wherein the second ring is configured to be affixed to the endoscopic surgical instrument.

10. The protective sleeve of claim 9, wherein the inner and outer tube portions define a pocket at the distal end portion of the flexible tube, and the distal ring and the second ring are located within the pocket.

11. The protective sleeve of claim 1, wherein the tube is coated with a lubricating material.

12. The protective sleeve of claim 1, wherein the distal end of the sleeve is movable relative to the proximal end of the tube.

13. A protective sleeve for use with an endoscopic surgical instrument, comprising:

a flexible tube having an opening at each of a proximal end and a distal end of the tube to accept the endoscopic surgical instrument, the tube having a length and being configured to cover at least a distal end portion of the endoscopic surgical instrument that reaches a treatment site in a body lumen;

a ring associated with the tube and separable from the tube, the ring configured to hold a portion of the tube relative to the surgical instrument; and a perforation located along at least a distal portion of the tube, wherein the tube is configured to peel back along the perforation from the distal end portion of the surgical instrument towards the proximal end of the tube so as to reveal the distal end portion of the surgical instrument.

14. The protective sleeve of claim 13, wherein the flexible tube is translucent.

15. The protective sleeve of claim 13, wherein the ring is located proximate one of the proximal and distal ends of the tube.

16. A protective sleeve for use with an endoscopic surgical instrument, comprising:

a flexible tube having an opening at each of a proximal end and a distal end of the tube to accept the endoscopic surgical instrument, the tube having a length and being configured to cover at least a distal end portion of the endoscopic surgical instrument that reaches a treatment site in a body lumen;

a perforation located along at least a distal portion of the tube, wherein the tube is configured to peel back along the perforation from the distal end portion of the surgical instrument towards the proximal end of the tube so as to reveal the distal end portion of the surgical instrument;

a first ring proximate one of the proximal and distal ends of the tube; and a second ring proximate the opposite end of the tube from the first ring.

17. The protective sleeve of claim 15, wherein the ring is elastic.

18. The protective sleeve of claim 13, wherein the distal end of the tube is movable relative to the proximal end of the tube.

19. The protective sleeve of claim 13, further comprising a perforation about a circumference of the tube.

20. A method for inserting an endoscopic surgical instrument into a body lumen, comprising:

providing a protective sleeve on and over a distal portion of the surgical instrument, the protective sleeve having a member to hold a portion of the sleeve relative to the surgical instrument, a distal end of the sleeve being moveable along the distal portion of the surgical instrument;

inserting the surgical instrument into the body lumen;

placing the distal portion of the surgical instrument proximate to a treatment site along the body lumen; and moving the distal end of the protective sleeve proximally toward the member to reveal the distal portion of the surgical instrument.

21. The method of claim 20, further comprising performing a surgical procedure, moving the distal end of the protective sleeve over the distal portion of the surgical instrument, and removing the surgical instrument from the body lumen.

22. A method for inserting an endoscopic surgical instrument into a body lumen, comprising:

providing a protective sleeve on and over a distal portion of the surgical instrument, a distal end of the sleeve being moveable along the distal portion of the surgical instrument;

inserting the surgical instrument into the body lumen;

placing the distal portion of the surgical instrument proximate to a treatment site along the body lumen;

severing a first ring located at a distal end of the protective sleeve, and moving a distal end of the protective sleeve toward a proximal end of the protective sleeve to reveal the distal portion of the surgical instrument.

23. The method of claim 22, further comprising tearing the protective sleeve along a length of the protective sleeve.

24. The method of claim 23, further comprising removing the protective sleeve from the surgical instrument.

25. The method of claim 24, further comprising removing the protective sleeve from the body lumen.

26. The method of claim 20, wherein the step of moving the distal end of the protective sleeve includes moving the distal end of the sleeve relative to the proximal end of the sleeve.

27. A method for inserting an endoscopic surgical instrument into a body lumen, comprising:

providing a protective sleeve over a distal portion of the surgical instrument, the protective sleeve having a ring separable from the sleeve and configured to hold a portion of the sleeve relative to the surgical instrument;

inserting the surgical instrument into the body lumen;

placing the surgical instrument in a desired location along the body lumen;

tearing the protective sleeve starting from a distal end of the protective sleeve along a length of the sleeve; and removing the torn sleeve from the body lumen.

28. A method for inserting an endoscopic surgical instrument into a body lumen, comprising:

providing a protective sleeve over a distal portion of the surgical instrument;

inserting the surgical instrument into the body lumen;

placing the surgical instrument in a desired location along the body lumen;

severing a first ring located at a first end of the protective sleeve;

tearing the protective sleeve starting from a distal end of the protective sleeve along a length of the sleeve; and removing the torn sleeve from the body lumen.

29. The method of claim 28, further comprising severing a second ring located at a second end of the protective sleeve.

30. The method of claim 27, further comprising tearing the protective sleeve about a circumference of the protective sleeve.

31. A method for inserting an endoscopic surgical instrument into a body lumen, comprising:

providing a protective sleeve over a distal portion of the surgical instrument;

inserting the surgical instrument into the body lumen;

severing a first ring located at a distal end of the protective sleeve;

placing the surgical instrument in a desired location along the body lumen; and moving a distal end of the protective sleeve toward a proximal end of the protective sleeve to reveal the distal portion of the surgical instrument.

32. The method of claim 31, further comprising tearing the protective sleeve along a length of the protective sleeve.

33. The method of claim 32, further comprising removing the protective sleeve from the surgical instrument.

34. The method of claim 33, further comprising removing the protective sleeve from the body lumen.

35. A medical device comprising:

an endoscopic instrument;

a protective sleeve on and over a distal portion of the endoscopic instrument, the sleeve having an opening at each end of a proximal end and a distal end of the sleeve; and a distal ring fixedly connected to the sleeve proximate the distal end of the sleeve and retractable in a proximal direction relative to the endoscopic instrument and thereby allow at least a portion of the sleeve to retract and reveal a distal end portion of the endoscopic instrument.

36. The device of claim 35, wherein the sleeve is coated with a lubricating material.

37. The device of claim 35, wherein the distal ring is retractable in the proximal direction relative to the proximal end of the sleeve.

38. The device of claim 35, further comprising at least one perforation located along at least a portion of the length of the sleeve.

39. The device of claim 35, wherein the sleeve is translucent.

40. The device of claim 35, further comprising a second ring positioned at a location along the sleeve in a direction proximal relative to the distal ring, the distal ring being retractable towards the second ring.

41. The device of claim 35, further comprising a perforation about a circumference of the sleeve.

42. The device of claim 35, further comprising a proximal ring proximate the proximal end of the sleeve.

43. The device of claim 42, further comprising a third ring located between the proximal and distal rings.

44. The device of claim 35, further comprising:

a second ring positioned at a location along the sleeve in a direction proximal relative to the distal ring, wherein the sleeve comprises an inner sleeve portion and an outer sleeve portion; and the distal ring is located at a point where the inner and outer sleeve portions meet.

45. The device of claim 44, wherein the second ring is configured to fix the sleeve onto the endoscopic instrument.

46. The device of claim 45, wherein the inner and outer sleeve portions define a pocket at the distal end portion of the flexible sleeve, and the distal ring and the second ring are located within the pocket.

* * * * *